USOO9993829B2

(12) United States Patent
Lee et al.

(10) Patent No.: US 9,993,829 B2
(45) Date of Patent: Jun. 12, 2018

(54) PLASMA PURIFICATION MODULE

(71) Applicant: CREATING NANO TECHNOLOGIES, INC., Tainan (TW)

(72) Inventors: Ji-Yung Lee, Tainan (TW); Min-Sheng Yu, Taitung County (TW); Guan-Hung Shen, Kaohsiung (TW); Andrew Ronaldi Tandio, Tainan (TW)

(73) Assignee: CREATING NANO TECHNOLOGIES, INC., Tainan (TW)

( * ) Notice: Subject to any disclaimer, the term of this patent is extended or adjusted under 35 U.S.C. 154(b) by 0 days. days.

(21) Appl. No.: 15/622,069

(22) Filed: Jun. 13, 2017

(65) Prior Publication Data

US 2018/0008989 A1   Jan. 11, 2018

(30) Foreign Application Priority Data

Jul. 11, 2016 (TW) .............................. 105121782 A

(51) Int. Cl.
*B03C 3/38* (2006.01)
*A61L 9/22* (2006.01)
*F24F 3/16* (2006.01)
*H01T 23/00* (2006.01)

(52) U.S. Cl.
CPC ........ *B03C 3/38* (2013.01); *A61L 9/22* (2013.01); *F24F 3/166* (2013.01); *H01T 23/00* (2013.01)

(58) Field of Classification Search
None
See application file for complete search history.

(56) References Cited

U.S. PATENT DOCUMENTS

2006/0214020 A1* 9/2006 Suda .................... A61L 2/22
239/3

FOREIGN PATENT DOCUMENTS

| TW | 339497 B | 9/1998 |
| TW | 200304343 A | 9/2003 |
| TW | 200901832 A | 1/2009 |
| TW | 201026342 A | 7/2010 |
| TW | 201117842 A | 6/2011 |
| TW | 201408966 A | 3/2014 |
| TW | 201516360 A | 5/2015 |

\* cited by examiner

*Primary Examiner* — Kishor Mayekar
(74) *Attorney, Agent, or Firm* — CKC & Partners Co., Ltd.

(57) ABSTRACT

A plasma purification module is described. The plasma purification module includes a first electrode plate, a second electrode plate, at least one long electrode and a catchment element. The first electrode plate is configured to be connected to a first electrode of a power supply. The second electrode plate is disposed over a surface of the first electrode plate, and is configured to be connected to a second electrode of the power supply, in which the second electrode plate has a channel. The long electrode is configured to form a discharge area. The long electrode is disposed on the surface of the first electrode plate and passes through the channel. The long electrode has a tip. The catchment element is disposed adjacent to the tip, and is configured to provide the discharge area with mist or water.

8 Claims, 5 Drawing Sheets

PLASMA PURIFICATION MODULE

RELATED APPLICATIONS

This application claims priority to Taiwan Application Serial Number 105121782, filed Jul. 11, 2016, which is herein incorporated by reference.

BACKGROUND

Field of Invention

The present invention relates to a purification module. More particularly, the present invention relates to a plasma purification module.

Description of Related Art

The influence of indoor air quality on healthy has become an issue of international concern. Every person spends about 80%-90% of a day on staying in the indoor environments including home, an office, or other buildings, such that the indoor air quality directly effects quality of life and work efficiency. The contaminants exist in the indoor environments includes particulate matters, peculiar smell, volatile and semi-volatile organic matters, formaldehyde, and microscopic organisms.

Commercial negative ion generators can generate ions, and the contaminants in the air can be decomposed into harmless water and oxides through a chemical reaction in a discharge area, thus achieving a purification effect of the air. However, a volume range of the discharge area generated by this technique is limited, such that a volume of the reaction area is limited. In addition, the ions have very short life, such that most of the positive ions and the negative ions in the discharge area are neutralized with each other, and thus it is futile for purification.

SUMMARY

Therefore, one objective of the present invention is to provide a plasma purification module, which uses atmospheric pressure plasma with mist or water provided by a catchment element to form an ion group. The water can be converted into mists in a nanometer scale under a high electric field, and the mists in the nanometer scale wrap the ions, such that the lifetime of the ions generated by the plasma can be prolonged, and neutralization reactions between the positive ions and the negative ions can be decreased, thereby broadening a reaction scope of the ions with contaminants, and thus effectively enhancing a purification effect.

According to the aforementioned objectives, the present invention provides a plasma purification module. The plasma purification module includes a first electrode plate, a second electrode plate, at least one long electrode, and a catchment element. The first electrode plate is configured to be connected to a first electrode of a power supply. The second electrode plate is disposed over a surface of the first electrode plate and is configured to be connected to a second electrode of the power supply, in which the second electrode plate has at least one channel. The long electrode is configured to form a discharge area, in which the long electrode is disposed on the surface of the first electrode plate and passes through the channel, and the long electrode has a tip. The catchment element is disposed adjacent to the tip and is configured to provide the discharge area with mist or water. The catchment element is disposed over the second electrode plate, the catchment element has at least one hole, and the at least one long electrode passes through the at least one channel and the at least one hole sequentially.

According to one embodiment of the present invention, the long electrode includes at least one needle electrode or a carbon brush.

According to one embodiment of the present invention, the catchment element includes a water absorbent material, a deliquescence salt, a thermoelectric cooler, or a cooling device.

According to one embodiment of the present invention, the catchment element is connected to the second electrode of the power supply.

According to one embodiment of the present invention, the second electrode plate and the second electrode are grounded.

According to one embodiment of the present invention, the plasma purification module further includes a high-voltage circuit board, in which the first electrode plate and the second electrode plate are electrically connected to the first electrode and the second electrode of the power supply via the high-voltage circuit board.

According to one embodiment of the present invention, a voltage difference between the first electrode plate and the second electrode plate substantially ranges from 3 kV to 9 kV.

According to the aforementioned objectives, the present invention further provides a plasma purification module. The plasma purification module includes a first electrode plate, at least one long electrode, a second electrode catchment plate, and a high-voltage circuit board. The first electrode plate is configured to be connected to a first electrode of a power supply. The long electrode is configured to form a discharge area, in which the long electrode is disposed on a surface of the first electrode plate, and the long electrode has a tip. The second electrode catchment plate is disposed over the surface of the first electrode plate and the tip of the long electrode, and is configured to be connected to a second electrode of the power supply and to provide the discharge area with mist or water. The first electrode plate and the second electrode catchment plate are electrically connected to the first electrode and the second electrode of the power supply via the high-voltage circuit board.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
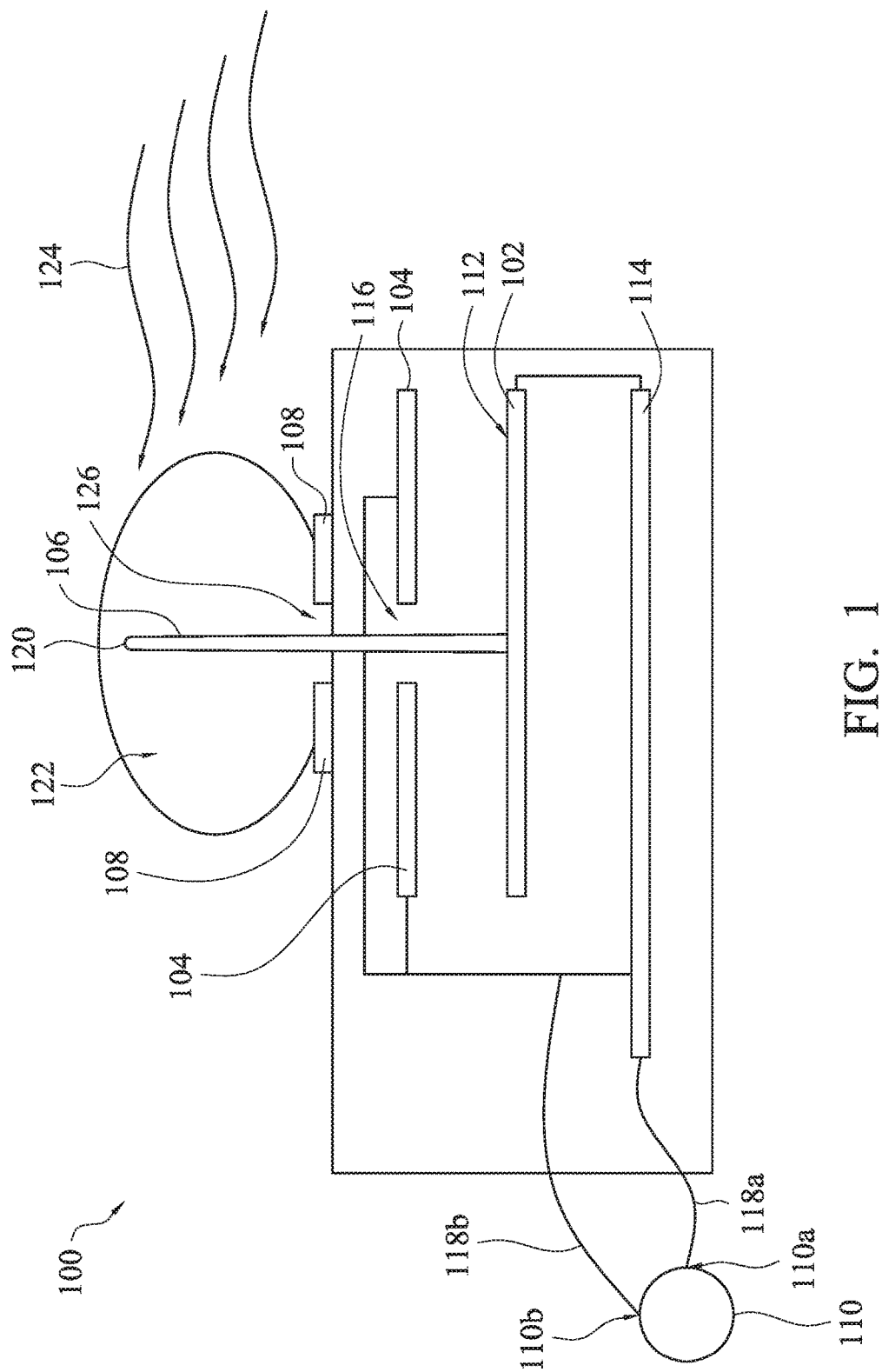
FIG. 1 is a schematic drawing of a plasma purification module in accordance with one embodiment of the present invention.

Referring to FIG. 1, FIG. 1 is a schematic drawing of a plasma purification module in accordance with one embodiment of the present invention. A plasma purification module 100 may be installed in an air-conditioning apparatus, such as an air conditioner, or an air-purifying apparatus, in which the plasma purification module 100 is preferably disposed on a path that the air flow outflows the apparatus to purify the gas using plasma before the gas flows out of the apparatus. The plasma purification module 100 is an atmospheric pressure plasma purification module due to the application concern. In the present embodiment, the plasma purification module 100 may mainly include a first electrode plate 102, a second electrode plate 104, at least one long electrode 106, and a catchment element 108.

As shown in FIG. 1, the first electrode plate 102 may be connected to a first electrode 110a of a power supply 110, in which the power supply 110 includes the first electrode 110a and a second electrode 110b, and the first electrode 110a and the second electrode 110b have different electrical potentials. The second electrode plate 104 is disposed over a surface 112 of the first electrode plate 102, and the second electrode plate 104 may be connected to the second electrode 110b of the power supply 110. In some examples, the first electrode 110a of the power supply 110 has a relatively higher electric potential, and the electric potential of the second electrode 110b is smaller than that of the first electrode 110a. For example, the second electrode 110b is grounded and has a grounding electric potential. In some exemplary examples, a voltage difference between the first electrode plate 102 and the second electrode plate 104 may range from about 3 kV to about 9 kV, and may preferably range from about 4 kV to about 6 kV.

Referring to FIG. 1 again, the second electrode plate 104 has at least one channel 116. In some exemplary examples, a quantity of the channel 116 of the second electrode plate 104 may correspond to a quantity of the long electrode 106. When the second electrode plate 104 has only one channel 116, the channel 116 may be in a shape of a hole, and the second electrode plate 104 is in a shape of a ring.

Referring to FIG. 1 again, the plasma purification module 100 may optionally include a high-voltage circuit board 114. The high-voltage circuit board 114 is connected to the first electrode 110a and the second electrode 110b of the power supply 110 respectively via wires 118a and 118b. The first electrode plate 102 and the second electrode plate 104 may be connected to the high-voltage circuit board 114, such that the first electrode plate 102 and the second electrode plate 104 can be electrically connected to the first electrode 110a and the second electrode 110b of the power supply 110 respectively via the high-voltage circuit board 114. Therefore, the power supply 110 can supply electric power to the first electrode plate 102 and the second electrode plate 104 by supplying electric power to the high-voltage circuit board 114. The power supply 110 may be a typical alternating current power supply (110V or 220V), or a direct current battery, and the high-voltage circuit board 114 can transform the alternating current of 110V (or the alternating current of 220V) or the low-voltage direct current into high-voltage direct current, so as to control a voltage difference between the first electrode plate 102 and the second electrode plate 104 within a desired range, such as from about 3 kV to about 9 kV. In some exemplary examples, the second electrode 110b of the power supply 110 has a ground electric potential, such that the second electrode plate 104 electrically connected to the second electrode 110b is grounded.

Referring to FIG. 1 again, the long electrode 106 is disposed on the surface 112 of the first electrode plate 102 and passes through the channel 116 of the second electrode plate 104. The long electrode 106 has a tip 120, in which the tip 120 passes through the channel 116 and is located over the second electrode plate 104. After the first electrode plate 102 and the second electrode plate 104 are electrified, the long electrode 106 discharges to form a discharge area 122, in which the discharging of the long electrode 106 mainly concentrates at the tip 120. In some exemplary examples, the long electrode 106 may include at least one needle electrode, or a carbon brush with a lot of bristles.

The discharge area 122 can be formed at the vicinity of the long electrode 106, and when the air 124 with organic contaminants, viruses, and germs passes through the discharge area 122, an ionization and oxidization reaction caused within the discharge area 122 can decompose the organic contaminants in the air 124 and can degenerate deoxyribonucleic acid (DNA) and capsomers of the germs and the viruses to exterminate the germs and the viruses, thereby achieving an effect of improving air quality. When the second electrode plate 104 of the plasma purification module 100 is grounded, a unlike charges attracting principle can be used. After particles of the air 124 are charged, the particles move to and are adhered to the grounded second electrode plate 104 under the effect of the coulomb force, such that the particles are removed from the air 124. In some examples, when the plasma purification module 100 is installed in any air-conditioning apparatus, a grounded plate may be additionally disposed at air outlet of the air-conditioning apparatus to catch the charged particles in the air 124 which has passes through the discharge area 122. In such examples, the second electrode plate 104 may not be a grounded plate.

The catchment element 108 is disposed adjacent to the tip 120 of the long electrode 106. In the embodiment, as shown in FIG. 1, the catchment element 108 is disposed over the second electrode plate 104, and the catchment element 108 has at least one hole 126, in which the long electrode 106 passes through the channel 116 of the second electrode plate 104 and the hole 126 of the catchment element 108 in sequence. Thus, the tip 120 of the long electrode 106 is located over the catchment element 108, and that is the catchment element 108 is located between the tip 120 and the second electrode plate 104. In some examples, the catchment element 108 may be disposed over the tip 120 of the long electrode 106, such that the catchment element 108 may not include any hole. A quantity of the hole 126 of the catchment element 108 may correspond to a quantity of the long electrode 106. In addition, the catchment element 108 is not connected to any power supply device. The catchment element 108 can provide the discharge area 122 with mist or water. In some exemplary examples, the catchment element 108 may include a water absorbent material, and the water absorbent material is provided with water by the air air-conditioning system which the plasma purification module 100 is disposed in, or by an additional water-supplying system. For example, the water absorbent material may be a sponge. In some other examples, the catchment element 108 may include a deliquescence salt, a thermoelectric cooler or other cooling device. The thermoelectric cooler or the cooling device can provide a local low temperature environment, and when a temperature of the surface of the catchment element 108 is lower than a dew-point temperature of the air 124, the moisture in the air 124 starts to condense, so as to raise humidity at the vicinity of the long electrode 106.

The catchment element 108 can raise humidity at the vicinity of the long electrode 106, such that the plasma discharging in the discharge area 122 of the long electrode 106 can decompose water and air to form ions, such as hydrogen ions, oxygen ions, hydroxide ions, and the likes, and the water can be converted into mists in a nanometer scale under a high electric field. The mists in the nanometer scale wrap the ions, such that the lifetime of the ions wrapped by the mists is longer than that of the free ions, and thus as the ions floats along the air stream of the air 124, the ions can contact more germs and viruses in the external air to degenerate protein structures of the germs and the viruses. Therefore, an effective area range of sterilization and improving of air quality can be greatly broadened. Furthermore, the catchment element 108 is separated from the discharging long electrode 106, such that it can prevent the long electrode 106 from being significantly corroded, thereby effectively increasing the lifetime of the long electrode 106.

Figure 2:
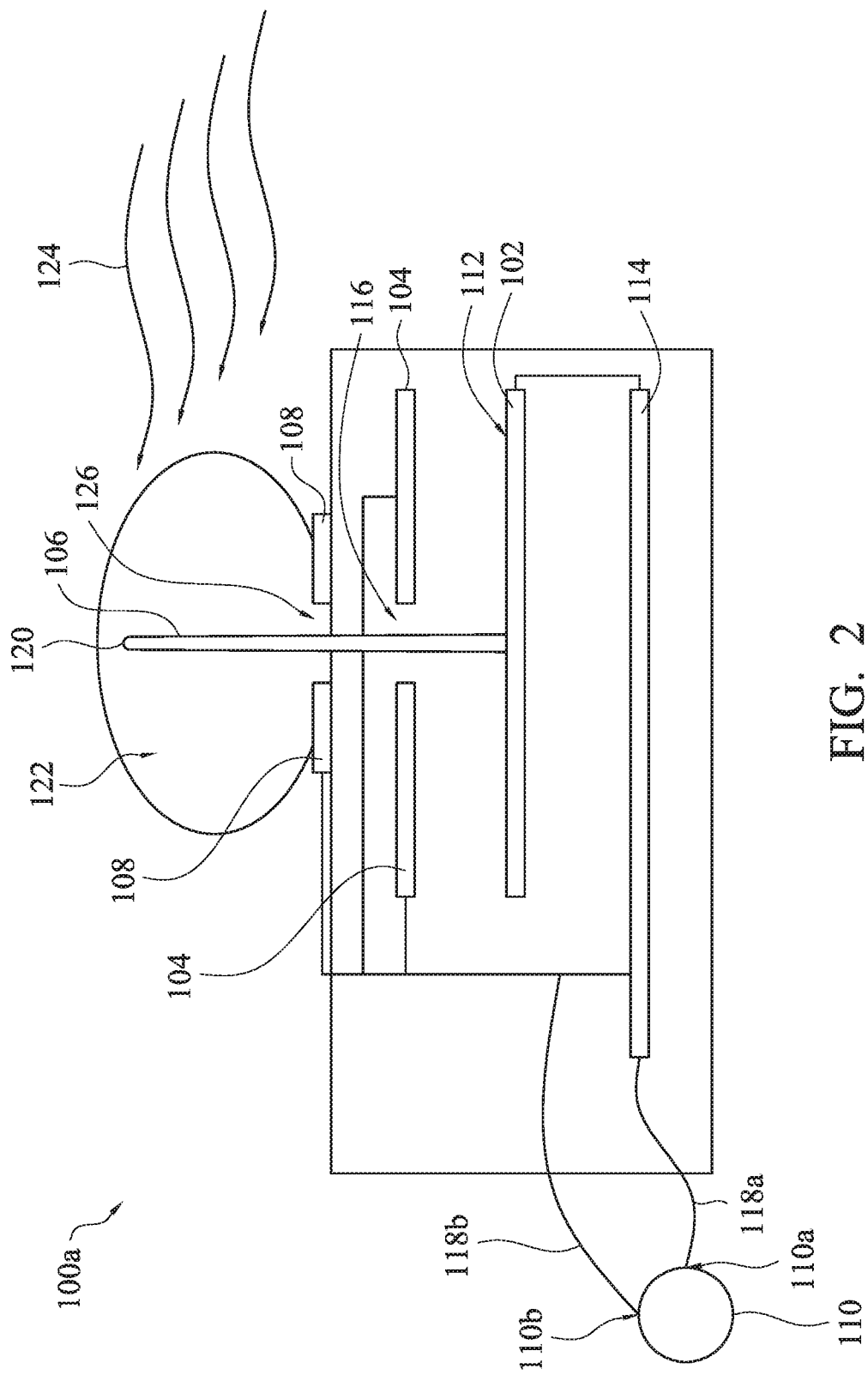
FIG. 2 is a schematic drawing of a plasma purification module in accordance with another embodiment of the present invention.

Referring to FIG. 2, FIG. 2 is a schematic drawing of a plasma purification module in accordance with another embodiment of the present invention. A structure of a plasma purification module 100a of the present embodiment is substantially similar to the plasma purification module 100 of the aforementioned embodiment, and a difference between the plasma purification modules 100a and 100 is that the plasma purification module 100 is not a water electrode system, and the plasma purification module 100a is a water electrode system, that is the catchment element 108 of the plasma purification module 100a is electrically connected to a power supply system. In some examples, the catchment element 108 of the plasma purification module 100a is connected to the second electrode 110b of the power supply 110. As a result, the catchment element 108, the second electrode plate 104, and the second electrode 110b of the power supply 110 have the same electric potential. For example, the catchment element 108, the second electrode plate 104, and the second electrode 110b of the power supply 110 are all grounded. In the embodiment, a material of the catchment element 108 is electrically conductible.

Figure 3:
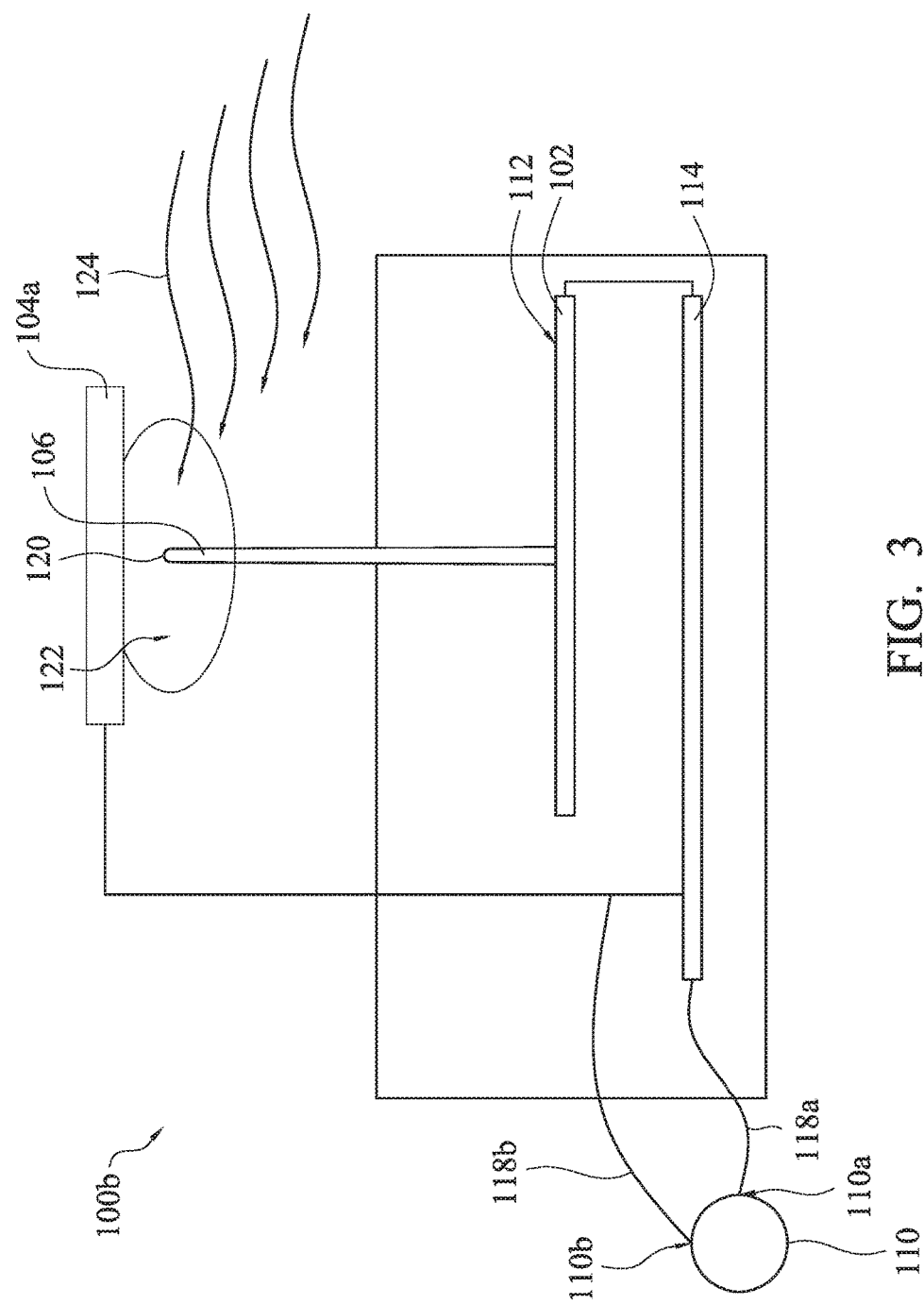
FIG. 3 is a schematic drawing of a plasma purification module in accordance with still another embodiment of the present invention.

Referring to FIG. 3, FIG. 3 is a schematic drawing of a plasma purification module in accordance with still another embodiment of the present invention. A structure of a plasma purification module 100b of the present embodiment is substantially similar to the plasma purification module 100a of the aforementioned embodiment, and differences between the plasma purification modules 100b and 100a are that the plasma purification module 100b uses a second electrode catchment plate 104a to replace the second electrode plate 104 and the catchment plate 108 of the plasma purification module 100a, and the second electrode catchment plate 104a is located over the tip 120 of the long electrode 106. The second electrode catchment plate 104a is located over the tip 120 of the long electrode 106, such that the second electrode catchment plate 104a may not include any channel or hole. In addition, the second electrode catchment plate 104a is electrically connected to the second electrode 110b of the power supply 110.

Figure 4:
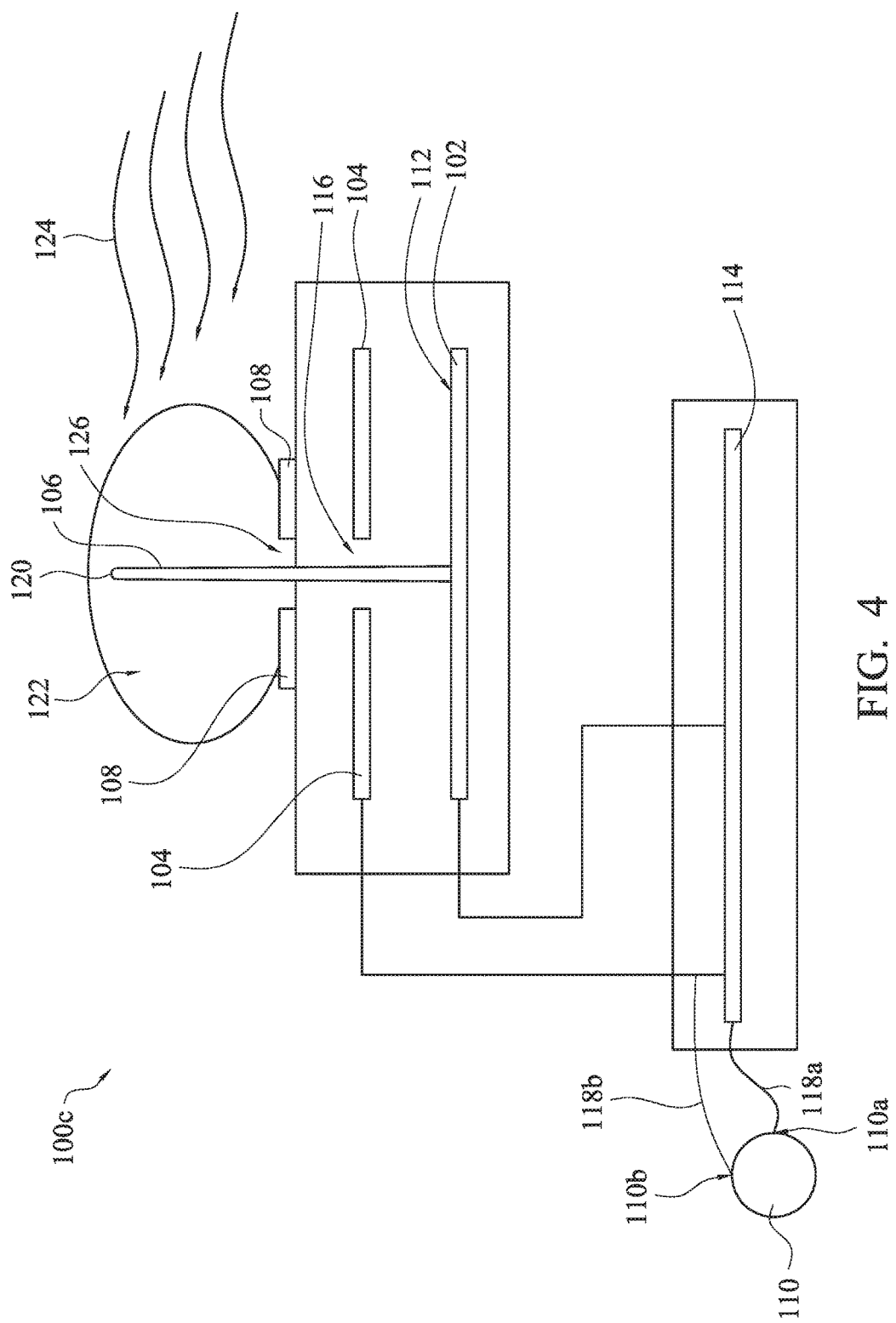
FIG. 4 is a schematic drawing of a plasma purification module in accordance with further another embodiment of the present invention.

Referring to FIG. 4, FIG. 4 is a schematic drawing of a plasma purification module in accordance with further another embodiment of the present invention. A structure of a plasma purification module 100c of the present embodiment is substantially similar to the plasma purification module 100 of the aforementioned embodiment, and a difference between the plasma purification modules 100c and 100 is that the plasma purification module 100c itself does not include a high-voltage circuit board 114, and the plasma purification module 100c is connected with a high-voltage circuit board 114 by being externally connected to the high-voltage circuit board 114. Thus, the plasma purification module 100c can be applied an apparatus set with the high-voltage circuit board 114.

Figure 5:
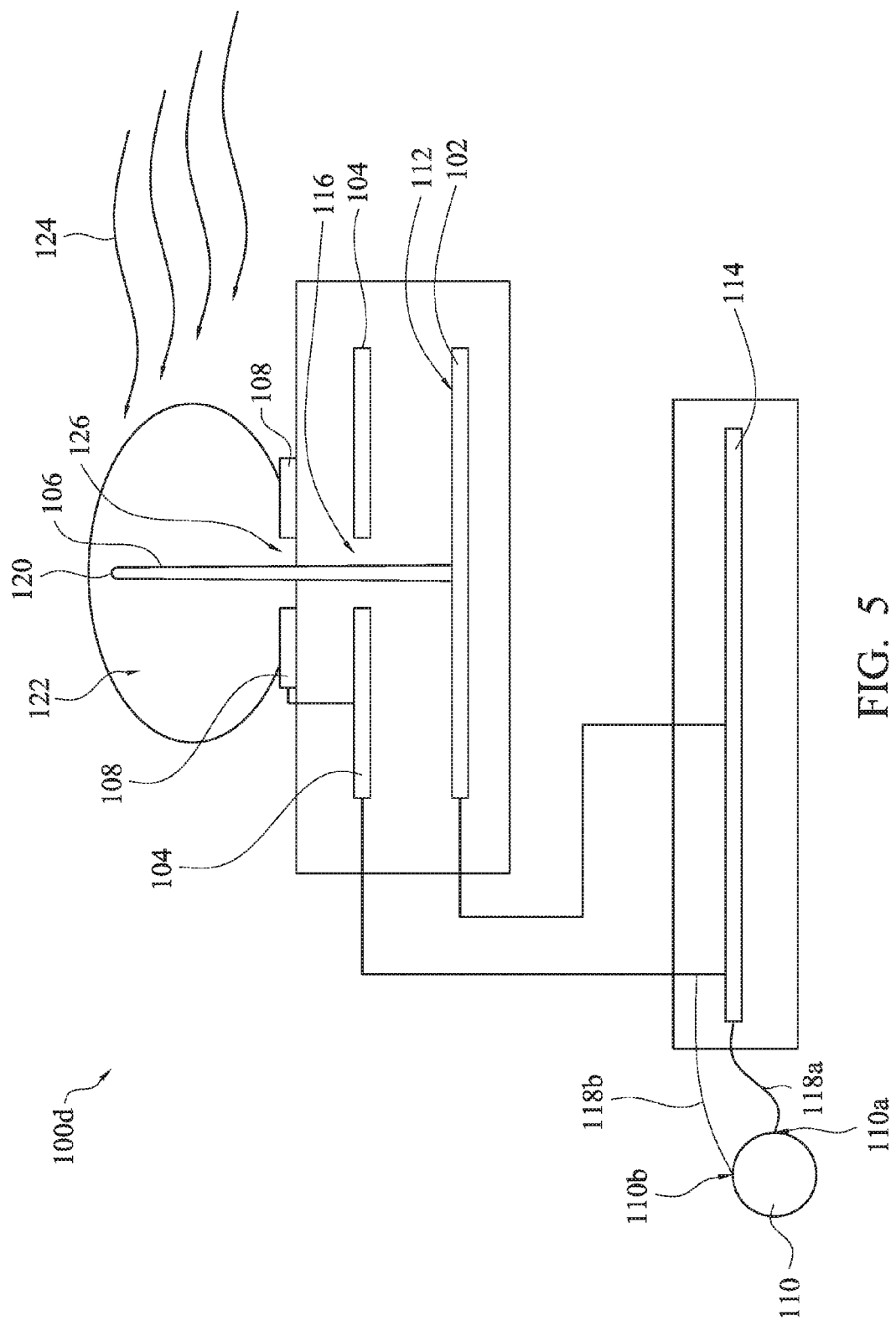
FIG. 5 is a schematic drawing of a plasma purification module in accordance with further another embodiment of the present invention.

Referring to FIG. 5, FIG. 5 is a schematic drawing of a plasma purification module in accordance with further another embodiment of the present invention. A structure of a plasma purification module 100d of the present embodiment is substantially similar to the plasma purification module 100a of the aforementioned embodiment, and a difference between the plasma purification modules 100d and 100a is that the plasma purification module 100d does not include a high-voltage circuit board 114, and the plasma purification module 100d is connected with a high-voltage circuit board 114 by being externally connected to the high-voltage circuit board 114. Thus, the plasma purification module 100d can be applied an apparatus set with the high-voltage circuit board 114.

According to the aforementioned embodiments, one advantage of the present invention is that a plasma purification module of the present invention uses atmospheric pressure plasma with mist or water provided by a catchment element to form an ion group. The water can be converted into mists in a nanometer scale under a high electric field, and the mists in the nanometer scale wrap the ions, such that the lifetime of the ions generated by the plasma can be prolonged, and neutralization reactions between the positive ions and the negative ions can be decreased, thereby broadening a reaction scope of the ions with contaminants, and thus effectively enhancing a purification effect.

Although the present invention has been described in considerable detail with reference to certain embodiments thereof, the foregoing embodiments of the present invention are illustrative of the present invention rather than limiting of the present invention. It will be apparent to those having ordinary skill in the art that various modifications and variations can be made to the present invention without departing from the scope or spirit of the invention. Therefore, the spirit and scope of the appended claims should not be limited to the description of the embodiments contained herein.

What is claimed is:

1. A plasma purification module, comprising:
a first electrode plate configured to be connected to a first electrode of a powersupply;
a second electrode plate disposed over a surface of the first electrode plate and configured to be connected to a second electrode of the power supply, wherein the second electrode plate has at least one channel;
at least one long electrode configured to form a discharge area, wherein the at least one long electrode is disposed on the surface of the first electrode plate and passes through the at least one channel, and the at least one long electrode has a tip; and
a catchment element disposed adjacent to the tip and configured to provide the discharge area with mist or water, wherein the catchment element is disposed over the second electrode plate, the catchment element has at least one hole, and the at least one long electrode passes through the at least one channel and the at least one hole sequentially.

2. The plasma purification module of claim 1, wherein the at least one long electrode comprises at least one needle electrode or a carbon brush.

3. The plasma purification module of claim 1, wherein the catchment element comprises a water absorbent material, a deliquescence salt, a thermoelectric cooler, or a cooling device.

4. The plasma purification module of claim 1, wherein the catchment element is connected to the second electrode of the power supply.

5. The plasma purification module of claim 1, wherein the second electrode plate and the second electrode are grounded.

6. The plasma purification module of claim 1, further comprising a high-voltage circuit board, wherein the first electrode plate and the second electrode plate are electrically connected to the first electrode and the second electrode of the power supply via the high-voltage circuit board.

7. The plasma purification module of claim 1, wherein a voltage difference between the first electrode plate and the second electrode plate substantially ranges from 3 kV to 9 kV.

8. A plasma purification module, comprising:
- a first electrode plate configured to be connected to a first electrode of a power supply;
- at least one long electrode configured to form a discharge area, wherein the at least one long electrode is disposed on a surface of the first electrode plate, and the at least one long electrode has a tip;
- a second electrode catchment plate disposed over the surface of the first electrode plate and the tip of the at least one long electrode, and configured to be connected to a second electrode of the power supply and to provide the discharge area with mist or water; and
- a high-voltage circuit board, wherein the first electrode plate and the second electrode catchment plate are electrically connected to the first electrode and the second electrode of the power supply via the high-voltage circuit board.

* * * * *